(12) United States Patent
House

(10) Patent No.: US 9,759,683 B1
(45) Date of Patent: Sep. 12, 2017

(54) MINIATURIZED ELECTROPHORESIS DEVICE WITH INTEGRATED ELECTROCHEMICAL DETECTION

(71) Applicant: Stephen D. House, St. Michael, MN (US)

(72) Inventor: Stephen D. House, St. Michael, MN (US)

(*) Notice: Subject to any disclaimer, the term of this patent is extended or adjusted under 35 U.S.C. 154(b) by 156 days.

(21) Appl. No.: 14/709,774

(22) Filed: May 12, 2015

(51) Int. Cl.
  *G01N 27/447* (2006.01)
  *G01N 27/417* (2006.01)

(52) U.S. Cl.
  CPC ..... *G01N 27/44791* (2013.01); *G01N 27/417* (2013.01)

(58) Field of Classification Search
  CPC .......................................... B03C 5/00–5/028
  See application file for complete search history.

(56) References Cited

U.S. PATENT DOCUMENTS

| 2004/0011650 A1* | 1/2004 | Zenhausern | ...... B01L 3/502746 204/547 |
| 2013/0217210 A1* | 8/2013 | Brcka | ...................... B03C 5/005 438/466 |

\* cited by examiner

*Primary Examiner* — J. Christopher Ball
(74) *Attorney, Agent, or Firm* — Dave Alan Lingbeck

(57) ABSTRACT

A miniaturized electrophoresis device with integrated electrochemical detection for detecting target molecules by electrochemical separation. The miniaturized electrophoresis device with integrated electrochemical detection includes a planar member having a top side and made of an inert substrate; and unit cells integrated and adjacently arranged consecutively upon the top side of the planar member and connectable to a power source to effect an electric potential across the unit cells to separate ionic target molecules from a solution deposited upon the planar member increasing signal to noise ratio.

8 Claims, 2 Drawing Sheets

MINIATURIZED ELECTROPHORESIS DEVICE WITH INTEGRATED ELECTROCHEMICAL DETECTION

BACKGROUND OF THE INVENTION

Field of the Invention

The present invention relates to electrophoresis devices and more particularly pertains to a new miniaturized electrophoresis device with integrated electrochemical detection for electrophoretically separating target molecules and electrochemically detecting and quantifying them.

Description of the Prior Art

The use of electrophoresis devices is known in the prior art. More specifically, electrophoresis devices heretofore devised and utilized are known to consist basically of familiar, expected and obvious structural configurations, notwithstanding the myriad of designs encompassed by the crowded prior art which have been developed for the fulfillment of countless objectives and requirements.

The prior art includes a capillary electrophoresis device, comprising a substrate; a first channel in the substrate, and having a buffer arm and a detection arm; a second channel in the substrate intersecting the first channel, and having a sample arm and a waste arm; a buffer reservoir in fluid communication with the buffer arm; a waste reservoir in fluid communication with the waste arm; a sample reservoir in fluid communication with the sample arm; and a detection reservoir in fluid communication with the detection arm. Another prior art includes an apparatus for conducting a microfluidic process and analysis, including at least one elongated microfluidic channel, fluidic transport means for transport of fluids through the microfluidic channel, and at least one thick-film electrode in fluidic connection with the outlet end of the microfluidic channel. Also, another prior art includes a microfluidic device having integrated components for conducting chemical operations. The components include electrodes for manipulating charged entities, heaters, electrochemical detectors, sensors for temperature, pH, fluid flow, and other useful components. The device may be fabricated from a plastic substrate such as, for example, a substantially saturated norbornene based polymer. The components are integrated into the device by adhering an electrically conductive film to the substrate. Further another prior art includes a microfabricated capillary electrophoresis chip which includes an integral thin film electrochemical detector for detecting molecules separated in the capillary.

While these devices fulfill their respective, particular objectives and requirements, the aforementioned patents are capillary base and do not disclose a new miniaturized electrophoresis device with integrated electrochemical detection for planar electrophoresis separation.

SUMMARY OF THE INVENTION

The general purpose of the present invention, which will be described subsequently in greater detail, is to provide a new miniaturized electrophoresis device with integrated electrochemical detection which has many of the advantages of the electrophoresis devices mentioned heretofore and many novel features that result in a new miniaturized electrophoresis device with integrated electrochemical detection which is not anticipated, rendered obvious, suggested, or even implied by any of the prior art electrophoresis devices, either alone or in any combination thereof. The present invention includes a planar member having a top side and made of an inert substrate; and unit cells integrated and adjacently arranged consecutively upon the top side of the planar member and connectable to a power source to effect an electric potential across the unit cells to separate ionic target molecules from a solution deposited upon the planar member increasing signal to noise ratio. None of the prior art includes the combination of the elements of the present invention.

There has thus been outlined, rather broadly, the more important features of the miniaturized electrophoresis device with integrated electrochemical detection in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new miniaturized electrophoresis device with integrated electrochemical detection which has many of the advantages of the electrophoresis devices mentioned heretofore and many novel features that result in a new miniaturized electrophoresis device with integrated electrochemical detection which is not anticipated, rendered obvious, suggested, or even implied by any of the prior art electrophoresis devices, either alone or in any combination thereof.

Still another object of the present invention is to provide a new miniaturized electrophoresis device with integrated electrochemical detection for detecting and quantifying target molecules by typical electrochemical means.

Still yet another object of the present invention is to provide a new miniaturized electrophoresis device with integrated electrochemical detection that has a symmetrical pattern for each unit cell to yield identical repeatable signal results.

Even still another object of the present invention is to provide a new miniaturized electrophoresis device with integrated electrochemical detection with 3 parallel detection filaments arranged for detecting and quantifying target molecules.

Even still another object of the present invention is to provide a new miniaturized electrophoresis device with integrated electrochemical detection with field electrodes used to provide the electric field to move ions.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

Figure 1:
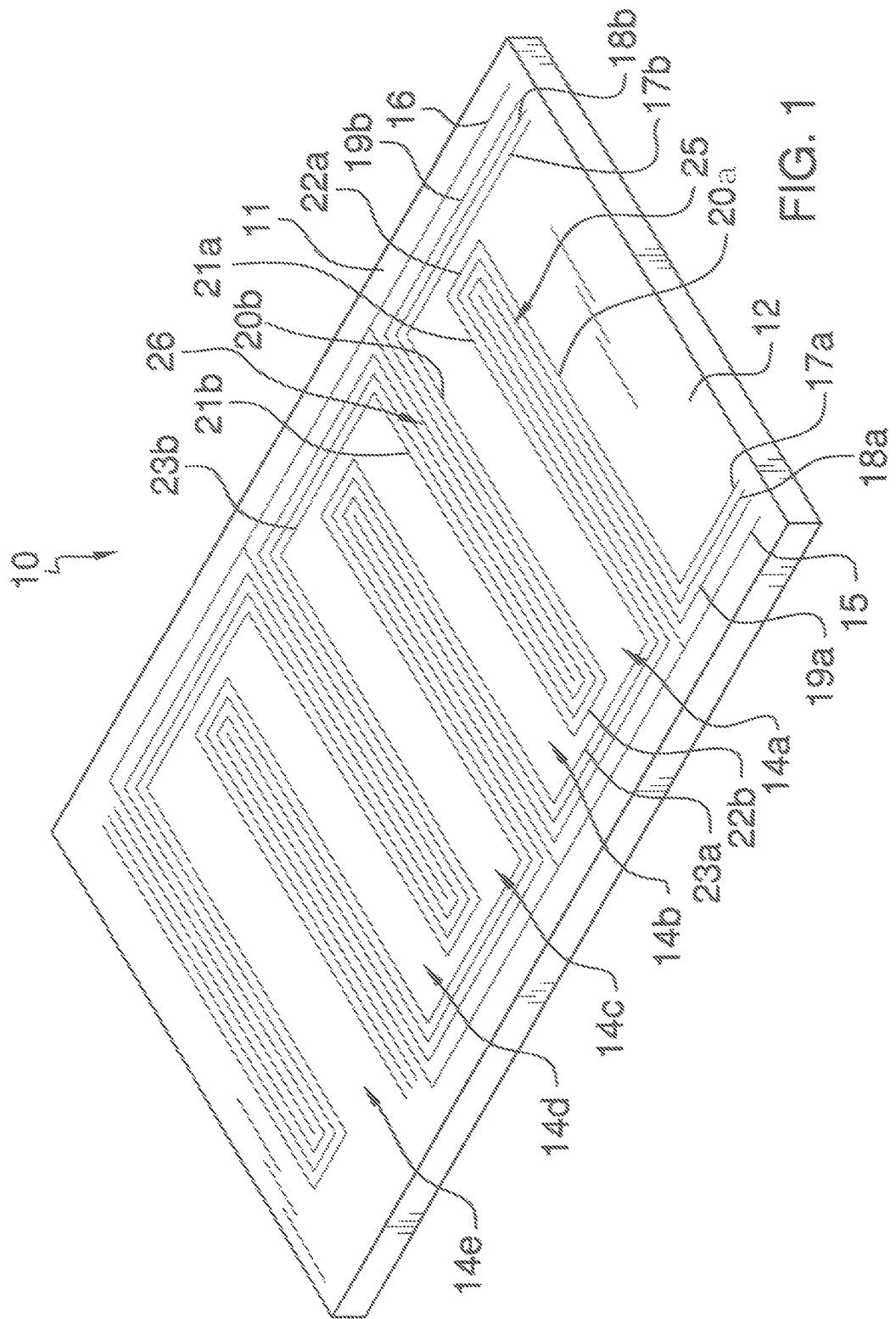
FIG. 1 is a top perspective view of a new miniaturized electrophoresis device with integrated electrochemical detection according to the present invention.
Figure 2:
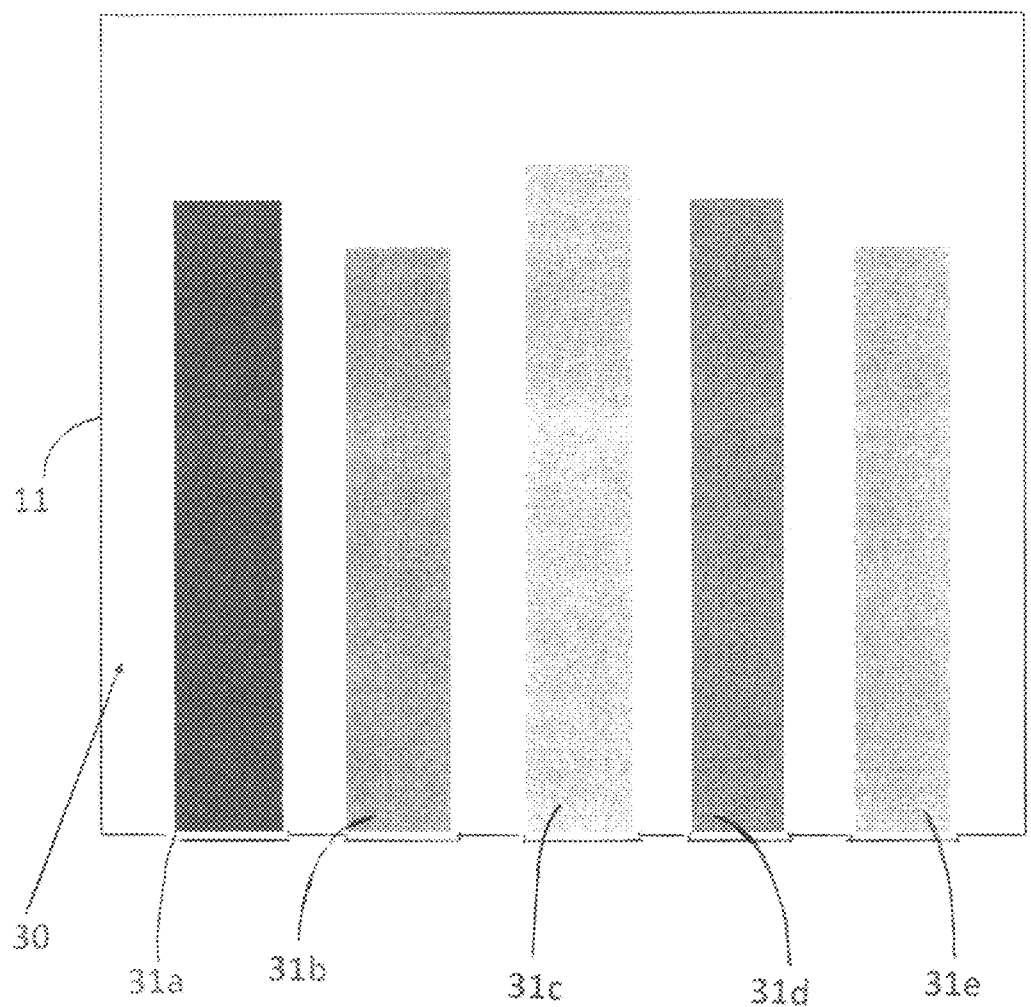
FIG. 2 is a schematic diagram of a planar member with a solution disposed on the planar member with bands of target molecules.

With reference now to the drawings, and in particular to FIGS. 1 and 2 thereof, a new miniaturized electrophoresis device with integrated electrochemical detection embodying the principles and concepts of the present invention and generally designated by the reference numeral 10 will be described. As best illustrated in FIGS. 1 and 2, the miniaturized electrophoresis device with integrated electrochemical detection 10 may generally comprise a planar member 11 such as a chip having a top side 12 and made of an inert substrate, and may further comprise unit cells 14a-e conventionally integrated and adjacently arranged consecutively upon the top side 12 of the planar member 11 and adapted to be connected to a power source to effect an electric potential across the unit cells 14a-e to separate ionic target molecules 31a-e from a solution 30 deposited upon the planar member 11 with the plurality of unit cells 14a-e increasing signal to noise ratio. Each of the unit cells 14a-e may include first and second field electrodes 15, 16 separated from one another with the electric potential capable of being applied between the first and second field electrodes 15, 16. Each of the first and second field electrodes 15, 16 may include detection filaments 17a-b, 18a-b, 19a-b conventionally disposed upon the planar member 11 and spaced apart and arranged parallel to one another. Each of the detection filaments 17a-b, 18a-b, 19a-b may extend continuously across and interconnecting the unit cells 14a-e. Each of the detection filaments 17a-b, 18a-b, 19a-b may be arranged symmetrically and serpentine upon and along a length of the planar member 11. Each of the detection filaments 17a-b, 18a-b, 19a-b may be arranged in symmetrical sections 25, 26 and may include linear segments 20a-b, 21a-b, 22a-b, 23a-b. Each of the symmetrical sections 25, 26 may include a first linear segment 20a-b and a second linear segment 21a-b spaced apart from and juxtaposed with and parallel to the first linear segment 20a-b. The linear segments 20a-b, 21a-b, 22a-b, 23a-b of each of the symmetrical sections 25, 26 of each of the detection filaments 17a-b, 18a-b, 19a-b may also include a first connecting segment 22a-b interconnecting the first and second linear segments 20a-b, 21a-b. The linear segments 20a-b, 21a-b, 22a-b, 23a-b may further include second connecting segments 23a-b interconnecting the symmetrical sections 25, 26. The symmetrical section 25 of the first field electrode 15 may be separated from and parallel to the symmetrical section 26 of the second field electrode 16. The detection filaments 17a-b, 18a-b, 19a-b of each of the first and second field electrodes 15, 16 may include a reference detection filament 17a-b, an anode detection filament 18a-b and a cathode detection filament 19a-b. The anode detection filaments 18a-b may be spaced between the reference detection filaments 17a-b and the cathode detection filaments 19a-b with the detection filaments 17a-b, 18a-b, 19a-b of the first and second field electrodes 15, 16 closest to one another being the reference detection filaments 17a-b.

The miniaturized electrophoresis device 10 may allow both the electrophoretic separation of ionic target molecules 31a-e and the electrochemical detection and quantitation of the separated target molecules 31a-e in the solution 30. Each of the unit cells 14a-e with the first and second field electrodes 15, 16 comprising the detection filaments 17a-b, 18a-b, 19a-b may be controlled to create an electric field in the solution 30. An electric potential difference may be applied between the first field electrode 15 and the second field electrode 16, creating an electric field which causes ionic target molecules 31a-e to migrate toward the field electrode 15, 16 of the opposite charge. An initial electric field may be necessary to align target molecules 31a-e to one of the first and second field electrodes 15, 16 on the miniaturized electrophoresis device 10. The electric field may be cycled with target molecules 31a-e migrating and forming target bands between the first and second field electrodes 15, 16. Each target band may migrate in the solution 30 at a rate inversely proportional to the molecular mass of the target molecule 31a-e and thus be separated from other target molecules 31a-e that have a different mass. The unit cells 14a-e act as detectors and signal collectors as target molecular bands pass over the cathode detection filament 19a-b and the anode detection filament 18a-b and are electrolyzed. The target molecules 31a-e in a solution mixture may be separated electrophoretically on the basis of molecular weight and detected electrochemically. This allows iterative operation across the unit cells 14a-e yielding repeatable, identical signal results that can be digitally stored and added together to increase overall signal and reduce signal-to-noise ratio as random noise between signal sets is cancelled. The detection filament dimensions and the separation distances between them within a unit cell 14a-e are important to optimize the performance of miniaturized electrophoresis device 10. The narrower the first and second field electrodes 15, 16, the narrower the initial bands of target molecules 31a-e that migrate through the solution 30, leading to better separation of the bands for detection. The narrower the cathode and anode detection filaments 18a-b, 19a-b, the more concentrated the detection signal will be as target molecules 31a-e pass over them and are electrolyzed. The greater the distance between the detection filaments 17a-b, 18a-b, 19a-b in the first and second field electrodes 15, 16, the greater the separation of target molecule bands during migration between them, since separation is time dependent. The closer the cathode detection filament 19a-b and the anode detection filament 18a-b are to their respective first and second field electrodes 15, 16, the better the separation of target molecule bands at the time of detection and signal collection, and thus the better the quality of signals originating from different molecules 31a-e. The lower the voltage difference between the first and second field electrodes 15, 16, the lower the risk of "fouling" of detection filament surfaces by unintended chemical reactions, or lifting of the detection filaments 17a-b, 18a-b, 19a-b from the planar member 11 thus destroying the circuit. The miniaturized electrophoresis device 10 may provide analysis of DNA, proteins and amino acids and analysis of metal ions or ionic metallo-organic compounds. The basic advantage in having the multiple unit cells 14a-e is enhanced signal strength. Also because of the symmetry within each unit cell 14a-e, the test may be repeated by switching/cycling the electric field over and over until the target molecules 31a-e have been electrolyzed and detected. Each trace would add an identical output and thus build signal, while reducing random noise because the random noise signals will tend to cancel out.

In use as illustrated in FIG. 2, the solution 30 with the target molecules 31a-e is deposited upon at least one of the unit cells 14a-e using a suitable applicator such as a pipette, and an electrical potential difference is effected across the at least one unit cell 14a-e, using the power source. Preferably, the solution 30 is deposited between the first and second field electrodes 15, 16 in the at least one of the unit ceils 14a-e. A potential difference is effected between the detection filaments 17a-b, 18a-b, 19a-b to detect target molecules separately migrating across the detection filaments 17a-b, 18a-b, 19a-b. The target molecules 31a-e are detected separately migrating across the planar member 11 in the at least one of the unit cells 14a-e. The target molecules 31a-e migrate and separate into distinctive identifiable bands from the first field electrode 15 to the second field electrode 16 in the at least one of the unit cells 14a-e due to the electrical potential difference between the first and second field electrodes 15, 16. The electrical potential difference may be effected upon and across the unit cells 14a-e. Thus, the target molecules 31a-e are further separated and identified as an electrical potential difference is effected upon and across the unit cells 14a-e with the target molecules 31a-e migrating and forming bands across the unit cells 14a-e.

Electrochemical detection of target molecules 31a-e as each molecule band crosses over the reference/anode/cathode detection filaments 17a-b, 18a-b, 19a-b. Time dependent amperometric signals may be collected and stored. Displaying as signal vs. time data will result in a time dependent trace showing signal peaks that correspond to the detection of individual molecules 31a-e. The relative areas under each peak will correspond to the amount of the respective molecule 31a-e present in the initial solution 30. Adding new data from repeated cycles, overall signal may increase, and the signal to noise ratio may be improved.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the miniaturized electrophoresis device with integrated electrochemical detection. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A miniaturized electrophoresis device with integrated electrochemical detection comprising:
  a planar member having a top side and made of an inert substrate; and
  unit cells integrated and adjacently arranged consecutively upon the top side of the planar member and adapted to be connected to a power source to effect an electric potential across the unit cells to separate ionic target molecules from a solution deposited upon the planar member increasing signal to noise ratio, wherein each of the unit cells includes first and second field electrodes separated from one another with the electric potential capable of being applied between the first and second field electrodes, wherein each of the first and second field electrodes includes detection filaments disposed upon the planar member and spaced apart and arranged parallel to one another, wherein each of the detection filaments extends continuously across and interconnecting the unit cells, wherein each of the detection filaments includes linear segments, wherein each of the detection filaments is arranged symmetrically and serpentine upon and along a length of the planar member.

2. The miniaturized electrophoresis device with integrated electrochemical detection as described in claim 1, wherein each of the detection filaments is arranged in symmetrical sections.

3. The miniaturized electrophoresis device with integrated electrochemical detection as described in claim 2, wherein each of the symmetrical sections include a first linear segment and a second linear segment spaced apart from and juxtaposed with and parallel to the first linear segment.

4. The miniaturized electrophoresis device with integrated electrochemical detection as described in claim 3, wherein the linear segments of each of the symmetrical sections of each of the detection filaments include a first connecting segment interconnecting the first and second linear segments.

5. The miniaturized electrophoresis device with integrated electrochemical detection as described in claim 4, wherein the linear segments further include second connecting segments interconnecting the symmetrical sections.

6. The miniaturized electrophoresis device with integrated electrochemical detection as described in claim 2, wherein the symmetrical sections of the first field electrode are separated from and parallel to the symmetrical sections of the second field electrode.

7. A method of using a miniaturized electrophoresis device comprising the steps of:
  providing a planar member having unit cells with detection filaments disposed upon the planar member and arranged in a symmetrical pattern and forming first and second field electrodes in each of the unit cells;
  depositing a solution with target molecules upon at least one of the unit cells;
  effecting an electrical potential difference across the at least one of the unit cells with a power source; and
  detecting the target molecules separately migrating across the planar member in the at least one of the unit cells.

8. The method of using the miniaturized electrophoresis device as described in claim 7, wherein the unit cells are arranged consecutively upon the planar member to enhance and increase signal strength and reduce noise.

* * * * *